US005891740A

United States Patent [19]

Di Cesare et al.

[11] Patent Number: 5,891,740
[45] Date of Patent: Apr. 6, 1999

[54] DETECTION OF LOW LEVEL HYDROPHOBIC ANALYTES IN ENVIRONMENTAL SAMPLES USING AGGLUTINATION REACTION CAPILLARY SLIDE TEST AND APPARATUS THEREFOR

[75] Inventors: Joseph L. Di Cesare, Redding, Conn.; Steven M. Rosen, Mountain Lakes, N.J.

[73] Assignees: The Perkin-Elmer Corporation, Norwalk, Conn.; Roche Diagnostic Systems, Inc., Branchburg, N.J.

[21] Appl. No.: 832,168

[22] Filed: Apr. 2, 1997

[51] Int. Cl.$^6$ ................................................. G01N 33/543
[52] U.S. Cl. .......................... 436/518; 436/548; 436/534; 436/536; 435/7.1; 422/99
[58] Field of Search .................................. 436/518, 548, 436/534, 536; 422/99; 210/635; 162/146; 435/7.1

[56] References Cited

U.S. PATENT DOCUMENTS

| | | | |
|---|---|---|---|
| 4,446,239 | 5/1984 | Tsuji et al. | 436/532 |
| 4,530,786 | 7/1985 | Dunbar et al. | 260/112 B |
| 4,596,695 | 6/1986 | Cottingham | 422/58 |
| 4,597,944 | 7/1986 | Cottingham | 422/73 |
| 4,775,515 | 10/1988 | Cottingham | 422/73 |
| 4,798,807 | 1/1989 | Vanderlaan et al. | 436/548 |
| 5,019,351 | 5/1991 | Schulz | 422/99 |
| 5,128,244 | 7/1992 | Poland et al. | 435/7.8 |
| 5,145,790 | 9/1992 | Mattingly et al. | 436/536 |
| 5,207,915 | 5/1993 | Hagen et al. | 210/635 |
| 5,236,826 | 8/1993 | Marshall | 435/7.92 |
| 5,290,517 | 3/1994 | Samuels et al. | 422/58 |
| 5,429,925 | 7/1995 | Vanderlaan et al. | 435/7.1 |
| 5,501,949 | 3/1996 | Marshall | 435/5 |
| 5,578,459 | 11/1996 | Gordon et al. | 135/29 |
| 5,627,080 | 5/1997 | Cheng et al. | 436/534 |
| 5,654,178 | 8/1997 | Fitzpatrick et al. | 435/70.21 |
| 5,688,370 | 11/1997 | Hagen et al. | 162/146 |
| 5,702,610 | 12/1997 | Hagen et al. | 210/670 |

FOREIGN PATENT DOCUMENTS

| | | | |
|---|---|---|---|
| 471570A1 | 2/1992 | European Pat. Off. | A61B 10/00 |
| WO97/25619 | 7/1997 | WIPO | G01N 33/53 |

OTHER PUBLICATIONS

"Screening for Drugs of Abuse with the Roche ONTRAK Assays", Journal of Analytical Toxicology, vol. 16, May/Jun. 1992.
"3M Empore™, Strontium Rad Disks", IBC Advanced Technologies, Inc., 1995.
"Protrans™ Affinity Disks", ICN Biomedicals, Inc.
Patent Abstracts of Japan, vol. 95 No. 2 Mar. 31, 1995 being an Abstract of JP 06 313062A.
Patent Abstracts of Japan, vol. 11 No. 202 Jun. 30, 1987 being an Abstract of JP 62 027004A.
Patent Abstracts of Japan, vol. 9 No. 317 Dec. 12, 1985 being an Abstract of JP 60 153903A.
Derwent WPI Abstract of JP 62 064371A.
Roberts, M.a et al, Anal. Chem., 1995, vol. 68, pp. 482–491.
Jockers, R. et al, J. of Immunol. Methods, 1993, vol. 163, pp. 161–167.
Schmidt, D.J. et al, J. Agric. Food. Chem., vol. 38, pp. 1763–1770, 1990.
Vanderlaan et al, Environ. Monitoring by Immunol. vol. 22(3), 1988, pp. 247–254.
Bier, F.F. et al, Sensors and Actuators vol B7, 1992, pp. 509–512.
Engle, S.W. et al, 1992, Superfund '92, #259046 pp 238–241.

*Primary Examiner*—James C. Housel
*Assistant Examiner*—Ginny Allen Portner
*Attorney, Agent, or Firm*—George W. Rauchfuss, Jr.

[57] ABSTRACT

Apparatus and method for detection of low levels of about 1 ppb of hydrophobic analyte in environmental samples using an enclosed permeable membrane enrichment device and agglutination reaction slide test apparatus.

18 Claims, 2 Drawing Sheets

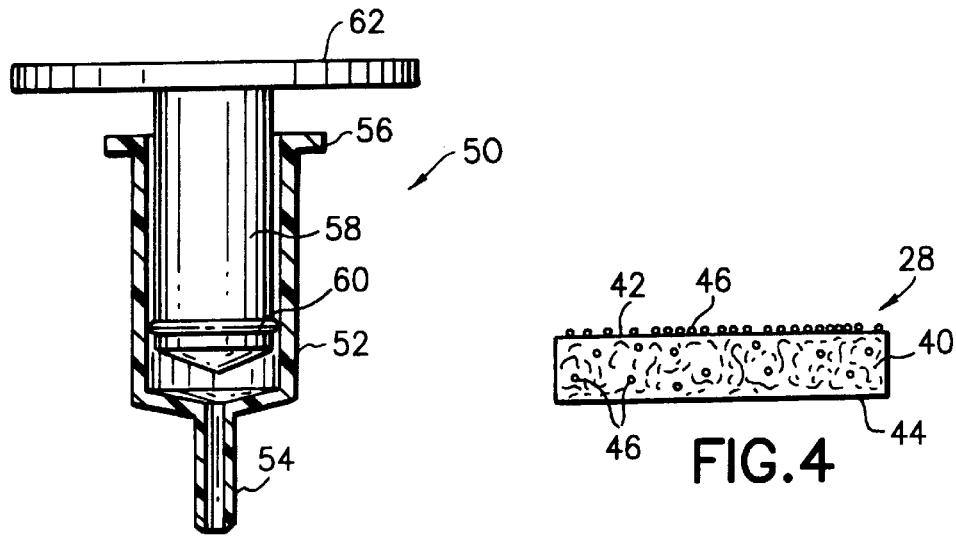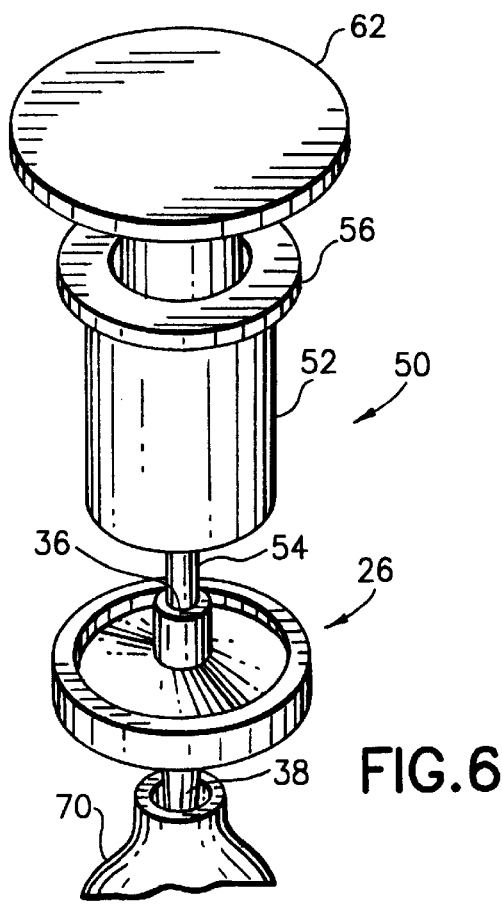

DETECTION OF LOW LEVEL HYDROPHOBIC ANALYTES IN ENVIRONMENTAL SAMPLES USING AGGLUTINATION REACTION CAPILLARY SLIDE TEST AND APPARATUS THEREFOR

FIELD OF THE INVENTION

This invention relates to apparatus and procedure for the detection of low levels, 10 ppb and more particularly 1 ppb or less, of hydrophobic analytes possibly present in environmental samples using agglutination reaction capillary slide test apparatus.

BACKGROUND OF THE INVENTION

Improved test apparatus has been provided for detection of substance for agglutination reactions. As examples of such improved test apparatus there can be mentioned U.S. Pat. Nos. 4,596,695; 4,597,944 and 4,775,515 of Hugh V. Cottingham and the agglutination slide device disclosed in U.S. Pat. No. 5,019,351 of Peter Schulz.

The agglutination test is based on latex agglutination-inhibition principles in which there is competition for binding to an antibody between the analyte and latex particles coated with an analyte analog or conjugate of the analyte. A sample is placed in the mixing well of a slide apparatus of the type disclosed in the aforementioned U.S. Pat. No. 5,019,351 along with the latex particles coated with the analyte analog or conjugate and the antibody. The mixture traverses the capillary path of the slide apparatus by capillary action to a viewing area. If there is no analyte in the sample, the latex particles with the analyte analog or conjugate form large clumps of particles (agglutinates) by binding to the antibody. However, when analyte is present in the sample, the analyte competes with the labeled latex particles for reaction with the antibody and the analyte preferentially binds to the antibody and inhibits or prevents reaction of the antibody with the labeled latex particles and thereby inhibits or prevents agglutination of the latex particles. Thus, the presence of agglutination of the latex particles is evidence of the absence of the analyte from the sample, whereas the absence of significant agglutination of the latex particles is evidence of the presence of the analyte in the sample, when the presence or absence of agglutination of the latex particles is visually observed in the viewing area of the slide apparatus.

Using the aforementioned technology and the agglutination slide apparatus disclosed in the aforesaid patents, test kits have been marketed for the easy, rapid determination of various biological substances such as hormones, tumor markers and the like and also for drugs of abuse, such as amphetamines, barbituates, cocaine, marijuana, morphines, phencyclidine and the like from biological samples, such as urine, blood or other body fluids. Such test apparatus and assay procedure have permitted easy and rapid field assays of biological fluids for such biological substances and drugs of abuse. Such rapid assays are able to be readily conducted in the field and require no instrumentation for analysis of the results. A visual qualitative result is observable in the slide viewing area, generally within about three to five minutes or less from the time of mixing the sample, labeled latex particles and antibody in the mixing well of the slide apparatus.

The use of such agglutination reaction slide apparatus has been highly beneficial, permitting on-site field analysis, that is, in a non-laboratory setting, by a simple, easy procedure without requiring other instrumentation. An example of such an assay test system for drugs of abuse is the ONTRAK test system sold by Roche Diagnostic Systems, Inc. of Somerville, N.J. Thus, this technology has replaced, at least in part, screening assay procedures previously required to be used, such as thin layer chromatography or liquid chromatography, enzyme immunoassay, fluorescence polarization immunoassay or radioimmuno-assay, requiring some type of instrumentation.

However, such agglutination reaction slide assay technology has been found to have an especially limiting drawback, namely that the concentration of analyte in the sample being analyzed must be at a relatively high concentration level of at least about 50 ppb or more in order to produce agglutination-inhibition to provide the desired visual result since generally only about a 11 $\mu$l sample volume in a total reaction volume of about 160 $\mu$l is able to be put into the mixing well of a slide apparatus. This drawback has prevented such agglutination slide reaction assay technology from being usable to detect analytes such as hydrophobic pesticides in environmental samples, such as water, effluent water, soil, sludge, manure wastes or sediments or the like, where the hydrophobic pesticide residues are or may be present only in very low concentration, such as about 1 ppb or less.

It has also previously been proposed to detect analytes by use of affinity chromatography techniques where an affinity membrane with a functional group and antibody attached directly to the membrane was permitted to come into intimate contact with the sample suspected of containing the analyte of interest. However, there is insufficient binding capacity for a number of reasons, including low surface binding area and loss of functionality of the antibody, and therefore generally only about 20% to about 40% of analyte is able to be recovered for detection and assay. Thus, such affinity chromatography techniques have also not provided a satisfactory field assay procedure for detection of 10 ppb or 1 ppb levels of pesticides and environmental toxins in environmental samples.

It is therefore highly desirable that an agglutination slide reaction assay system be available for quick, easy, in-the-field assays of environmental samples containing low level of analytes such as hydrophobic pesticides or other hydrophobic organic toxins.

SUMMARY OF THE INVENTION

The invention provides an improved agglutination reaction slide assay system and procedure for detection of low level hydrophobic analytes in environmental samples and a device for use in such system and procedure.

With the present invention, the agglutination reaction slide apparatus of the type disclosed in the aforementioned patents can now be employed to detect hydrophobic analytes present in environmental samples at levels below 10 ppb, even below 1 ppb or less. This is accomplished by means of a novel sample enrichment procedure utilizing a sample enrichment device along with agglutination-inhibition assay procedures in an agglutination reaction slide apparatus of the type disclosed in the aforementioned U.S. Pat. No. 5,019,351, the disclosure of which is incorporated herein by reference thereto.

In accordance with the invention there is provided a method for detecting the presence of a hydrophobic analyte in an environmental sample, in an amount of 10 ppb or less, especially in an amount of 1 ppb or less, wherein said method comprises:

(1) providing a determinable volume of the environmental sample;

(2) providing a permeable membrane in a liquid tight housing, the housing having an inlet port to a first surface of the membrane and an outlet port from a second, opposite surface of the membrane, said permeable membrane having pores or interstices therein and having silica particles coated with an aliphatic hydrocarbon hydrophobic phase located on the first surface of the permeable membrane;

(3) introducing the determinable volume of said sample, under a pressure differential, into the inlet port for travel through the permeable membrane and out the outlet port, with hydrophobic analyte in the environmental sample binding to the hydrophobic phase coated on the silica particles;

(4) thereafter, employing a volume of eluting solvent which is a fractional part of said determinable volume of sample, eluting analyte from the coated particles out the outlet port into a container as a concentrated hydrophobic analyte solution having a concentration of the hydrophobic analyte of at least about 50 ppb;

(5) introducing into and mixing in a receiving well of an agglutination reaction slide assay device (a) said concentrated hydrophobic analyte solution, (b) particles coated with an analyte analog or conjugate thereof, and (c) antibody to the hydrophobic analyte, introducing this mixture from the receiving well into a capillary track region of the slide assay device and permitting the mixture to traverse the capillary track region to a viewing region of the slide assay device; and (6) visually determining the absence or presence of hydrophobic analyte in the determinable volume of sample by observing the presence or absence, respectively, of significant agglutinated particles in the viewing region of the slide assay device.

BRIEF DESCRIPTION OF THE DRAWINGS

The invention will be described in detail in the following illustrative embodiment with reference to the drawings, in which:

FIG. 4 is an enlarged cross-sectional view of a membrane element of FIG. 3;

FIG. 5 is a partial cross-sectional view of a pressure differential providing device for use in the assay procedure of this invention; and FIG. 6 is a partial cross-sectional view of apparatus for preparing a concentrated analyte solution for use in the assay procedure of this invention.

DETAILED DESCRIPTION OF THE INVENTION

Figure 1:
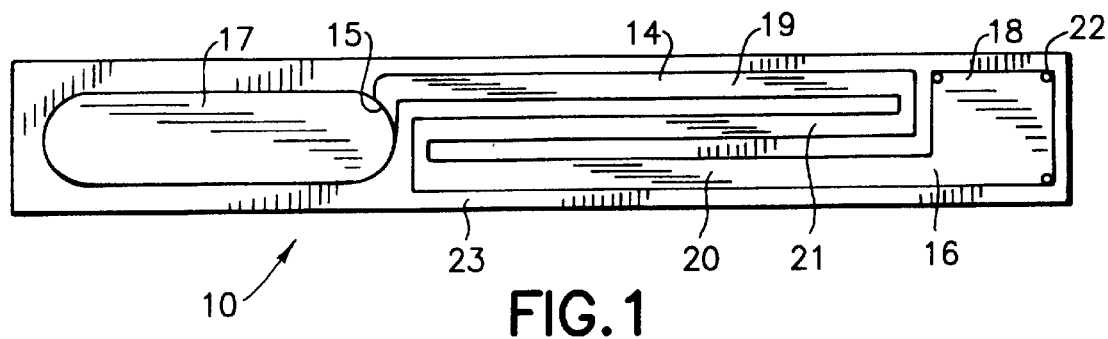
FIG. 1 is a plan view of an agglutination reaction slide assay device for agglutination tests of samples according to this invention.

This invention provides a ready and reliable field agglutination reaction assay for detection of hydrophobic analytes, particularly organic analytes such as pesticides, and polyaromatic organic compounds and other organic toxins, that are present in environmental samples at very low concentrations of about 1 ppb or less. This invention enables a field assay to be conducted in less than about 10 minutes to determine if an environmental sample contains the low level hydrophobic analyte being assayed.

The assay procedure of this invention is especially suitable for use in assaying any type of field environmental sample, such as, for example, water, effluent water, soil, sludge, wastes or sediments and the like, where the hydrophobic analyte may be present in amounts of about 1 ppb or less. The assay procedure can be employed to assay for any suitable hydrophobic analyte in the environmental sample. Of particular interest are pesticides, polyaromatic carcinogenic materials, and other organic toxins. For example, the improved assay procedure of this invention can be employed to assay for pesticides such as atrazine, aldrin, $\alpha$-BHC, $\beta$-BHC, $\gamma$-BHC, $\delta$-BHC, 4,4'-DDD, 4,4'-DDE, 4,4'-DDT, dieldrin, endosulfan I, endosulfan II, endosulfan sulfate, endrin, endrin aldehyde, endrin ketone, heptachlor, heptachlor epoxide, methoxychlor and the like, and polyaromatic carcinogen materials such as polychlorinated biphenyls, polychlorinated polyphenyls and PCP.

The agglutination reaction assay can be conducted on a suitable agglutination reaction slide assay device known in the art, such as that disclosed in the aforementioned U.S. Pat. No. 5,019,351 and illustrated in FIG. 1. The assay test element is represented by the general reference numeral 10. The test element comprises a receiving and mixing well 17 where a sample to be analyzed for analyte and appropriate reagents including antibody to the analyte and particles coated with an analyte analog or conjugate are mixed. The mixture is then permitted to enter a serpentine-shaped capillary reaction track 14 through upstream capillary entrance 15. The mixture proceeds along track 14 through upstream capillary region 19, intermediate capillary region 21 and downstream capillary region 20, exiting the capillary track by downstream capillary exit 16, entering a viewing or observation region in the form of viewing well 18. Viewing region 18 can be provided with bores 22 for venting the viewing region. A wall 23 extends around receiving area 17, viewing area 18 and capillary track region 14 to provide a fluid-tight bonding around these regions.

Figure 2:
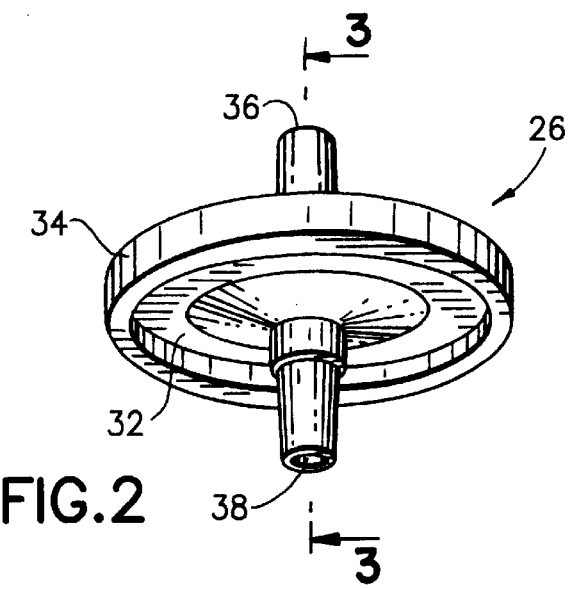
FIG. 2 is a perspective view of a permeable membrane in a fluid tight housing for use in this invention.
Figure 3:
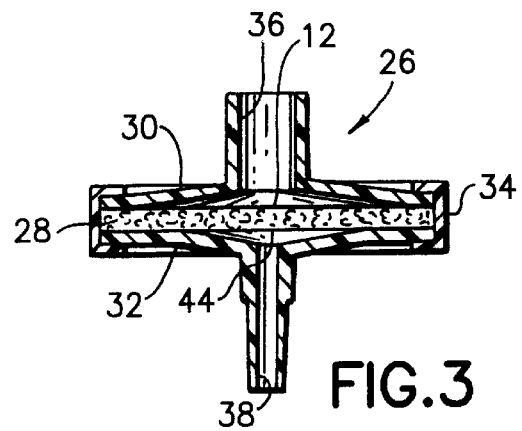
FIG. 3 is a cross-sectional view along line 3—3 of FIG. 2.

Before an environmental sample containing less than about 10 ppb, especially less than about 1 ppb of suspected hydrophobic analyte can be assayed in the reaction slide device of FIG. 1, the sample must be enriched or concentrated. Shown in FIGS. 2, 3 and 4 is an element for such a sample enrichment device, indicated generally by reference numeral 26. The element 26 comprises a suitable porous or permeable membrane 28 housed in the enrichment element and held between an inlet cap 30 and an outlet cap 32 by a retainer housing 34. Inlet cap 30 is provided with a generally centrally located inlet port 36 and outlet cap 32 is provided with a generally centrally located outlet port 38. Retainer housing 34 provides a fluid-tight housing around the inlet cap 30, permeable membrane 28 and outlet cap 32. The permeable membrane 28 is shown in greater detail in FIG. 4.

The membrane 28 is a disc 40 made of a permeable solid phase material which itself is inert to the hydrophobic analyte to be analyzed. The membrane disc 40 has a top surface 42 and a bottom surface 44 with holes or interstices therethrough. Particles 46, particularly silica particles coated with an aliphatic hydrocarbon hydrophobic phase, such as a $C_{18}$ aliphatic hydrocarbon, and attached to the top surface 42 of the membrane disc 40.

The pores or interstices of the membrane disc 40 will be smaller in size or diameter than the diameter of the coated particles 46. For example, the silica particles may generally have a diameter of from about 10 to 50 $\mu$m, preferably from about 40 to 50 $\mu$m, and the pores or interstices will generally be in the range of from about 0.4 to about 45 $\mu$m. The disc can be composed of any suitable substance inert to the reactants, such as, for example, paper, glass fiber, cotton, cellulose, cellulose acetate and synthetic polymeric material such as polytetrafluoroethylene, polyethylene, polypropylene, polyvinylidene fluoride and the like. A preferred membrane disc will be about 25 mm in diameter and have a capacity of at least 10 $\mu$g analyte, most preferably a glass fiber membrane disc of said size.

The aliphatic hydrocarbon hydrophobic phase can be any suitable aliphatic hydrocarbon, particularly those of $C_{10}$ to $C_{20}$ and especially a $C_{18}$ phase. $C_{18}$ coated silica particles on membranes are commercially available and sheets of said membrane may be cut into appropriately sized membrane discs and put into suitable fluid tight enrichment devices of this invention, as hereinbefore described.

The syringe 50 comprises a tubular housing 52 having at one end a centrally located conduit 54 for aspiration of material into and expiration of material from the housing. At the opposite end the tubular housing terminates in a shoulder 56. Located within housing 52 is a movable tubular piston 58 held in fluid tight relationship to the interior of tubular housing 52 by a sealing means 60, such as an O-ring. External of housing 52 piston 58 is provided with a suitable handle 62 for manual aspiration and expiration of material.

The membrane disc 40 with the coated silica particles located on the top surface of the disc is able to bind substantially all the hydrophobic analyte in the sample being processed through the enrichment device leading to at least about 88% or more, generally about 95% to 100% recovery of the hydrophobic analyte, compared to the about 20 to 40% recovery hydrophobic analyte usually obtained with antibody or affinity reagent bound directly to membranes.

Thereafter, an environmental sample containing less than about 10 ppb, preferably less than about 1 ppb of hydrophobic analyte, is aspirated into a syringe 50, the syringe attached to inlet port 36 and the environmental sample is expelled into enrichment device 26. Analyte in the sample binds to the aliphatic hydrocarbon hydrophobic phase coated particles which are on the top surface of the disc 40 while the fluid in the sample permeates the disc and flows out the outlet port 38 into a suitable collection vessel or container 70.

The analyte bound to the coated particles on the membrane disc 40 is then eluted with a small amount of elution solvent from a similar syringe 50 or squeezable container introduced into inlet pore 36 of enrichment device 28 to unbind hydrophobic analyte from the coated particles and elute the freed analyte out outlet port 38 into a suitable collection vessel or container 70. The elution solvent must be one that is compatible with and does not interfere with the agglutination reaction occurring in the slide apparatus, possess sufficient viscosity, similar to water, to permit movement of the reaction mixture in the slide apparatus and have no deleterious effects on antibody binding to analyte in the agglutination reaction slide. As examples of such suitable eluting solvents, there may be mentioned, for example, methanol or a solution of methanol, ethylene glycol, polyvinylpyrrolidone and sodium chloride, especially a solvent solution of about 60% methanol (v/v), about 40% ethylene glycol (v/v) about 4% polyvinyl pyrrolidone (w/v) and about 2% NaCl (w/v).

The small amount of elution solvent employed is a small, fractional volume part compared to the volume of environmental sample introduced into the enrichment device. For example, use of a 50 ml sample containing the hydrophobic analyte at a concentration of 1 ppb and use of 1 ml of elution solvent enables one to obtain about a 50-fold concentration factor so that the eluted 1 ml sample contains hydrophobic analyte at a concentration of about 50 ppb.

After the sample has been suitably enriched or concentrated in the foregoing manner, about 11 $\mu$l of the concentrated analyte solution is introduced into the receiving/mixing well 17 of slide apparatus 10 along with particles coated with an analyte analog or conjugate thereof and antibody to the hydrophobic analyte of interest and any necessary reaction buffers. This mixture is introduced to the capillary track region 14 through upstream inlet 15 and permitted to traverse the serpentine capillary track 19, 21, 20 to downstream exit 16 and into viewing region 18. If no analyte of interest was present in the environmental sample, and thus in the enriched solution thereof, the antibody will react with the analyte analog or conjugate in the capillary track causing agglutination of the particles. However, if hydrophobic analyte of interest was present in the environmental sample, and thus in the enriched solution thereof, the hydrophobic analyte of interest will bind to its antibody and prevent or inhibit the antibody from reacting with the analog or conjugate of the coated latex particles thus preventing or inhibiting particle agglutination.

Observation of the viewing area, after traverse of the sample and reagents through the capillary track, will enable a result to be visually determined: positive for analyte=no agglutination; negative for analyte=agglutination.

The assay procedure as just described is a relatively simple procedure requiring no special instrumentation and thus is readily conducive to quick field assays, i.e. assays in a non-laboratory environment, such as in nature or offices or homes or the like. Generally, the whole assay procedure including both the enrichment steps and the agglutinate reaction test can be conducted in about 10 minutes or less, generally about 5 minutes or less for the sample enrichment phase and 5 minutes or less for the agglutination reaction test phase.

Moreover, all the materials and devices needed for the assay procedure are easily produced, inexpensive and can be readily disposed of in an environmental acceptable manner.

All that is required to do a field assay for a hydrophobic analyte present in an environmental sample at a level of 10 ppb or less, particularly 1 ppb or less, is an enrichment device with a membrane having appropriately coated particles on the front surface of the membrane, one or more syringes and collection containers, the agglutination reaction slide device and the appropriate reagents, such as eluting solvent latex particles having an analyte or conjugate bound thereto, antibody for the analyte and any reaction buffer required or considered necessary.

The invention is further exemplified by the following illustrative example of assays for the hydrophobic pesticide atrazine.

EXAMPLE

An enrichment device of this invention having a $C_{18}$ silica particles on the top surface of a glass fiber membrane disc is provided. Employing a syringe, 20 ml of pond water, suspected to contain 10 ppb atrazine (i.e. 200 ng atrazine total) was passed through the $C_{18}$ membrane disc to capture the atrazine. Thereafter, the atrazine captured on the $C_{18}$ membrane disc was eluted with 1 ml eluting solvent comprising about 60% methanol (w/v), about 40% ethylene glycol (v/v), about 4% polyvinyl pyrrolidone (w/v) and about 2% NaCl (w/v) and the 1 ml of eluent collected in a collection bottle as an enriched analyte sample. Analysis of the enriched analyte sample revealed that 175 ng (88%) of atrazine from the sample had been recovered.

Assay of such an enriched analyte solution is conducted according to this invention by placing about 11 $\mu$l of the concentrated atrazine analyte solution, about 50 $\mu$l atrazine-BSA conjugated latex particles, about 50 $\mu$l antibody to atrazine, and about 50 $\mu$l buffer in the receiving and mixing well of an agglutination reaction slide apparatus of the type illustrated in FIG. 1, mixing the reagents in said well, introducing the mixture into the capillary track and permitting the reacting mixture to flow into the viewing area of the slide. Absence of agglutinated latex particles in the viewing confirms the presence of atrazine in the environmental water solution. In contradistinction, if the environmental water sample containing 1 ppb atrazine had been subjected to the same agglutination reaction assay without the enrichment procedure, the assay would have resulted in agglutination of the latex particles in the slide, falsely indicating the absence of atrazine in the environmental water solution.

With the foregoing description of the invention, those skilled in the art will appreciate that modifications may be made to the invention without departing from the spirit thereof. Therefore, it is not intended that the scope of the invention be limited to the specific embodiments illustrated and described.

We claim:

1. A method for detecting the presence of a hydrophobic analyte present in an environmental sample in an amount of 10 ppb or less, said method comprising:

(1) providing a determinable volume of said environmental sample;

(2) providing a permeable membrane in a liquid tight housing, said housing having an inlet port to a first surface of the membrane and an outlet port from a second, opposite surface the membrane, said permeable membrane having pores or interstices therein and having silica particles coated with an aliphatic hydrocarbon hydrophobic phase located on the first surface and entrapped in the pores or interstices of the permeable membrane;

(3) introducing said determinable volume of sample under a pressure differential into the inlet port for travel through the permeable membrane and out the outlet port, with analyte in the sample binding to the aliphatic hydrocarbon hydrophobic phase coated on the silica particles;

(4) thereafter, employing a volume of eluting solvent which is a fractional part of the said determinable volume of sample and comprises a solution of methanol, ethylene glycol, polyvinyl pyrrolidone and NaCl, eluting analyte from the coated silica particles out the outlet port into a container as a concentrated analyte solution having a concentration of the analyte of at least about 50 ppb;

(5) introducing into and mixing in a receiving well of an agglutination reaction slide assay device (a) said concentrated analyte solution, (b) particles coated with an analyte analog or conjugate thereof, and (c) antibody to the analyte, introducing this mixture from the receiving well into a capillary track region of the slide assay device and permitting the mixture to traverse the capillary track region to a viewing region of the slide assay device; and (6) visually determining the absence or presence of the hydrophobic analyte in the determinable volume of environmental sample by observing the presence or absence, respectively, of significant agglutinated latex particles in the viewing region of the slide assay device.

2. A method according to claim 1 wherein the pores and interstices of the permeable membrane are within the range of from about 0.4 to 45 $\mu$m and the coated particles located on the first surface of the permeable membrane are within the range of about 10 to 50 $\mu$m.

3. A method according to claim 2 wherein the permeable membrane is a glass fiber membrane.

4. A method according to claim 2 wherein the coated particles are $C_{18}$ coated particles.

5. A method according to claim 1 wherein the analyte is an organic pesticide.

6. A method according to claim 5 wherein the analyte is atrazine.

7. A method according to claim 1 wherein the sample is an environmental sample, the analyte is atrazine, the coated particles are $C_{18}$ coated particles within the range of about 40 to 50 $\mu$m, the permeable membrane is a glass fiber membrane having pores and interstices in the range of from about 0.4 to 45 $\mu$m and the fractional volume of the eluting solvent is no greater than about 1/50 of the determinable volume of the environmental sample.

8. A method according to claim 1 wherein the eluting solvent is selected from the group consisting of a solution of about 60% methanol (v/v), about 40% ethylene glycol (v/v), about 4% polyvinyl pyrrolidone (w/v) and about 2% NaCl (w/v).

9. A method according to claim 7 wherein the eluting solvent is selected from the group consisting of a solution of about 60% methanol (v/v), about 40% ethylene glycol (v/v), about 4% polyvinyl pyrrolidone (w/v) and about 2% NaCl (w/v).

10. A method for concentrating a hydrophobic analyte present in an environmental sample in an amount of 10 ppb or less, said method comprising:

(1) providing a determinable volume of said environmental sample;

(2) providing a permeable membrane in a liquid tight housing, said housing having an inlet port to a first surface of the membrane and an outlet port from a second, opposite surface of the membrane, said permeable membrane having pores or interstices therein and having silica particles coated with an aliphatic hydrocarbon hydrophobic phase located on the first surface of the permeable membrane;

(3) introducing said determinable volume of sample under pressure differential into the inlet port for travel through the permeable membrane and out the outlet port, with analyte in the sample binding to the aliphatic hydrocarbon hydrophobic phase coated on the silica particles; and (4) thereafter, employing a volume of eluting solvent which is a fractional part of the said determinable volume of sample and comprises a solution of methanol, ethylene glycol, polyvinyl pyrrolidone and NaCl, eluting analyte from the coated silica particles out the outlet port into a container as a concentrated analyte solution having a concentration of the analyte of at least about 50 ppb.

11. A method according to claim 10 wherein the pores and interstices of the permeable membrane are within the range of from about 0.4 to 45 $\mu$m and the coated particles located on the first surface of the permeable membrane are within the range of about 0.8 to 1.0 $\mu$m.

12. A method according to claim 11 wherein the permeable membrane is a glass fiber membrane.

13. A method according to claim 11 wherein the coated particles are $C_{18}$ coated silica particles.

14. A method according to claim 10 wherein the analyte is an organic pesticide.

15. A method according to claim 14 wherein the analyte is atrazine.

16. A method according to claim 10 wherein the sample is an environmental sample, the analyte is atrazine, the coated particles are $C_{18}$ silica particles within the range of about 40 to 50 µm, the permeable membrane is a glass fiber membrane having pores and interstices in the range of from about 0.4 to 45 µm and the fractional volume of the eluting solvent is no greater than about 1/50 of the determinable volume of the environmental sample.

17. A method according to claim 10 wherein the eluting solvent is selected from the group consisting of a solution of about 60% methanol (v/v), about 40% ethylene glycol (v/v), about 4% polyvinyl pyrrolidone (w/v) and about 2% NaCl (w/v).

18. A method according to claim 16 wherein the eluting solvent is selected from the group consisting of a solution of about 60% methanol (v/v), about 40% ethylene glycol (v/v), about 4% polyvinyl pyrrolidone (w/v) and about 2% NaCl (w/v).

* * * * *